(12) United States Patent
Fukuhira et al.

(10) Patent No.: US 7,915,028 B2
(45) Date of Patent: *Mar. 29, 2011

(54) TISSUE REGENERATION SUBSTRATE, COMPLEX THEREOF WITH CELLS, AND METHOD FOR ITS PRODUCTION

(75) Inventors: Yukako Fukuhira, Tokyo (JP); Masaya Ito, Tokyo (JP); Hiroaki Kaneko, Tokyo (JP); Yoshihiko Sumi, Tokyo (JP); Masatsugu Shimomura, Hokkaido (JP); Masaru Tanaka, Hokkaido (JP)

(73) Assignee: Teijin Limited, Osaka (JP)

( * ) Notice: Subject to any disclaimer, the term of this patent is extended or adjusted under 35 U.S.C. 154(b) by 22 days.

This patent is subject to a terminal disclaimer.

(21) Appl. No.: 10/580,029

(22) PCT Filed: Nov. 19, 2004

(86) PCT No.: PCT/JP2004/017637
§ 371 (c)(1),
(2), (4) Date: May 19, 2006

(87) PCT Pub. No.: WO2005/049104
PCT Pub. Date: Jun. 2, 2005

(65) Prior Publication Data
US 2007/0112438 A1    May 17, 2007

(30) Foreign Application Priority Data

Nov. 21, 2003 (JP) .................................. 2003-391935

(51) Int. Cl.
*C12M 3/00* (2006.01)
*A01N 1/02* (2006.01)
(52) U.S. Cl. ................... 435/284.1; 435/1.1; 435/40.51; 435/180; 435/395
(58) Field of Classification Search .................. None
See application file for complete search history.

(56) References Cited

U.S. PATENT DOCUMENTS

| 5,716,413 | A | 2/1998 | Walter et al. |
| 6,197,061 | B1 | 3/2001 | Masuda et al. |
| 6,818,018 | B1 * | 11/2004 | Sawhney ................... 623/11.11 |
| 2002/0187105 | A1 * | 12/2002 | Zou et al. ........................ 424/45 |

FOREIGN PATENT DOCUMENTS

| EP | 1 616 584 A1 | 1/2006 |
| JP | 7-135961 A | 5/1995 |
| JP | 2001-157574 A | 6/2001 |
| JP | 2001-293081 A | 10/2001 |
| JP | 2002-335949 A | 11/2002 |
| JP | 2002-345455 A | 12/2002 |
| WO | WO 2004/089434 A1 | 10/2004 |

OTHER PUBLICATIONS

Nishikawa et al. Materials Sci. and Eng. C8-9: 495-500; 1999.*
Watanabe et al. Biomacromolecules 3:1109-1114; 2002.*
Nishikawa et al. Mat. Res. Soc. Symp. Proc. 724:N11.7.1-N11.7.6; 2002.*
Watanabe et al., Stereocomplex Formation by Enantiomeric Poly(lactic acid) Graft-Type Phospholipid Polymers for Tissue Engineering, Biomacromolecules, vol. 3, No. 5, 2002, pp. 1109-1114.
Nishikawa T. et al.; The Chemical Society of Japan, 2001, vol. 80th, p. 128.
Nishikawa T. et al., Polymer Processing, 2001, vol. 50, No. 1, p. 10-15.
Fukuhira Y et al.; Biodegradable honeycomb-patterned film composed of poly(lactic acid) and dioleoylphosphatidylethanolamine; Biomaterials, Elsevier Science Publishers, vol. 27, No. 9, Mar. 1, 2006, pp. 1797-1802.
Sato K et al.; Seibunkaisei Kobunshi o Mochiita Takosei scaffold no Kokei Seigyo ni yoru Saibo Secchaku. Keitai no Henka (Preparation of the honeycomb patterned porous films of biodegradable polymer for tissue engineering scaffolds); 20020101, vol. 83, No. 2, Jan. 1, 2002, p. 958.

* cited by examiner

Primary Examiner — James (Doug) Schultz
(74) Attorney, Agent, or Firm — Sughrue Mion, PLLC

(57) ABSTRACT

A tissue regeneration substrate comprising a film with a honeycomb structure composed primarily of a polymer compound and a phospholipid. A tissue regeneration complex comprising the tissue regeneration substrate and cells held in the tissue regeneration substrate. The substrate is particularly suitable for regeneration of cartilage tissue, and allows growth of cartilage tissue in a three-dimensional fashion.

15 Claims, 3 Drawing Sheets

\* : P<0.05
\*\*\* : P<0.001

TISSUE REGENERATION SUBSTRATE, COMPLEX THEREOF WITH CELLS, AND METHOD FOR ITS PRODUCTION

TECHNICAL FIELD

The present invention a tissue regeneration substrate comprising a film having a honeycomb structure composed mainly of a polymer compound and a phospholipid, as well as to a complex thereof with cells and a method for its production.

BACKGROUND ART

Much attention has been given to the fact that cellular activity can be controlled by the minute patterns and three-dimensional structures of material surfaces, and such techniques have been the subject of numerous recent reports in the field of tissue engineering. The development of technologies for forming minute structures with the optimal size, surface structure and spatial creation for cells has come to play an pivotal role in achieving freer design of biological tissues.

For example, cartilage tissue contains no blood vessels, nerves or lymphatic ducts and therefore has poor regenerative capacity. Consequently, damaged sites are not regenerated and they lose their original function. Known clinical conditions involving loss of articular cartilage include diseases such as osteoarthritis and rheumatoid arthritis, and injury-induced articular cartilage damage. Artificial cartilage replacement surgery is performed for repair of such poorly regenerable cartilage, but because artificial cartilage includes metals and high molecular polymers it is susceptible to abrasion, loosening, infection and the like. Another strategy employed is transplantation of chondrocytes, but once damaged cartilage can only be regenerated as fibrocartilage, which is biochemically and dynamically inferior to the original hyaline cartilage. Therefore, a recent tissue engineering technique that is being actively researched is chondrocyte transplantation utilizing a scaffold with a three-dimensional structure in order to maintain the properties of cells.

One such technique is disclosed in Japanese Unexamined Patent Publication No. 2001-293081, as a cartilage transplant material having chondrocytes embedded in a collagen gel. However, if collagen is not handled at low temperature it gels and can no longer mix with cells, while its gel strength is also weak.

U.S. Pat. No. 6,197,061 discloses a method of growing chondrocytes in an alginate gel. However, the alginate gel is decomposed after use for cell growth and therefore in practice performs no function as a scaffold for injection of chondrocytes into affected areas.

Also, Japanese Unexamined Patent Publication No. 2001-157574 discloses the cell culturing substrate of a honeycomb structured film comprising a biodegradable polymer and an amphipathic polymer, but this publication nowhere refers to a cell culturing substrate and chondrocytes in a biodegradable film with a honeycomb structure comprising a phospholipid.

Furthermore, Japanese Unexamined Patent Publication No. 2002-335949 describes a method of forming a three-dimensional aggregate of hepatic tissue or myocardial tissue using the cell culturing substrate of a honeycomb structured film comprising a biodegradable polymer and an amphipathic polymer, but this method involves forming a multilayer structure by growing cells on both sides of the cell culturing substrate, whereas the cells themselves do not grow in a three-dimensional structure.

DISCLOSURE OF THE INVENTION

It is an object of the present invention to provide a tissue regeneration substrate. It is another object of the invention to provide a complex of the tissue regeneration substrate with cells.

It is yet another object of the invention to provide a method for producing the complex of the tissue regeneration substrate with cells.

Other objects and advantages of the invention will become apparent from the detailed explanation which follows.

According to this invention, the aforementioned objects and advantages are achieved, firstly, by a tissue regeneration substrate comprising a film with a honeycomb structure having an average cavity inner diameter from 0.1 to 20 μm, composed mainly of a polymer compound and a phospholipid.

The aforementioned objects and advantages of the invention are also achieved, secondly, by a complex of cells and a tissue regeneration substrate comprising a film with a honeycomb structure having an average cavity inner diameter from 0.1 to 20 μm, composed mainly of a polymer compound and a phospholipid.

The tissue regeneration substrate of the invention is a substrate suitable for regeneration of, in particular, cartilage tissue. By utilizing a film with a highly biocompatible honeycomb structure according to the invention, the film itself, though two-dimensional, serves as a cartilage tissue regeneration substrate which is similar to a three-dimensional scaffolding, whereby chondrocytes may be cultured on the tissue regeneration substrate to yield a cell/tissue regeneration substrate complex with cartilage tissue grown in a three-dimensional structure.

Cells other than chondrocytes can also be cultured on the honeycomb film disclosed by this invention to effectively form tissue in a three-dimensional structure.

The tissue regeneration substrate of the invention can provide a space for satisfactory cell growth of cells other than chondrocytes. As an example, a honeycomb film comprising a polymer compound and a phospholipid as disclosed by this invention can provide a more satisfactory space for excellent metabolic activity of cells grown thereon, than is possible with a film having a honeycomb structure of the type reported in the prior art.

Because the surface of the tissue regeneration substrate of the invention has a honeycomb structure, it has less cell adhesion area than a smooth film, and therefore cell growth is inhibited, a substrate is produced and the same effect is exhibited as a three-dimensional scaffold. The tissue regeneration substrate has a two-dimensional structure and is therefore easily manageable for easier cell seeding and the like, while the maintained cell density is high to allow cell culture to be easily and efficiently carried out.

BEST MODE FOR CARRYING OUT THE INVENTION

Figure 1:
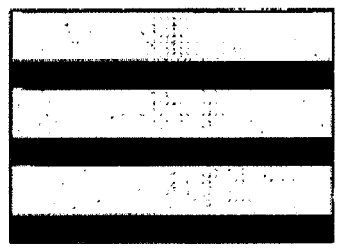
FIG. 1 is a schematic drawing of a laminate of complexes comprising a cartilage regeneration substrate and chondrocytes cultured on the substrate, according to the invention.

The present invention will now be described in greater detail. The examples and the explanation which follow serve merely for illustration of the invention, and are not intended to restrict the scope of the invention in any way. All other modes of the invention falling under the gist of the invention are also implied within its scope.

The polymer compound composing the film of the invention is preferably a biodegradable polymer. Preferred biodegradable polymers from the standpoint of solubility in organic solvents include polylactic acid, (lactic acid-glycolic acid) copolymer, polyhydroxybutyric acid, polycaprolactone, biodegradable aliphatic polyesters such as polyethylene adipate and polybutylene adipate and aliphatic polycarbonates such as polybutylene carbonate and polyethylene carbonate; these may also be copolymers or mixtures. Particularly preferred among these are polylactic acid, (lactic acid-glycolic acid) copolymer, polycaprolactone and (lactic acid-caprolactone) copolymer.

As examples of polymer compounds other than biodegradable polymers there may be mentioned polystyrene and vinyl-based polymers such as polyvinyl alcohol, poly(ethylene-covinyl acetate) and poly(hydroxyethyl methacrylate), and their copolymers, and condensed polymers such as poly(carbonates), poly(urethanes), nylon and the like, as well as their copolymers.

The source of the phospholipid composing the film of the invention is not important, and the phospholipid may be one extracted from animal tissue or one produced by artificial synthesis. The phospholipid is preferably at least one type selected from the group consisting of phosphatidylethanolamine, phosphatidylcholine, phosphatidylserine, phosphatidylglycerol and their derivatives. It is more preferably a phosphatidylethanolamine, and even more preferably L-α-phosphatidylethanolamine-dioleoyl.

Using a phospholipid allows control of the contact angle of the honeycomb structure film by adjusting the concentration of the phospholipid, in order to fabricate a more satisfactory honeycomb structure film having a more desirable contact angle for cell adhesion.

The compositional ratio of the polymer compound and the phospholipid is preferably 1:1-1000:1 by weight. It is more preferably 10:1-500:1 and even more preferably 50:1-200:1.

The film may also contain other components such as softeners or drugs so long as the object of the invention is not hindered.

Since fabrication of a film with a honeycomb structure according to the invention requires formation of fine water droplets on the polymer solution, the organic solvent used must be non-aqueous. As examples of such solvents there may be mentioned halogen-based organic solvents such as chloroform and methylene chloride, aromatic hydrocarbons such as benzene, toluene and xylene, esters such as ethyl acetate and butyl acetate, non-aqueous ketones such as methyl isobutyl ketone, and carbon disulfide. These organic solvents may be used alone, or a plurality of solvents may be combined for use as a mixed solvent.

The solution concentration including the polymer compound and phospholipid dissolved in the solvent is preferably 0.01-10 wt % and more preferably 0.05-5 wt %. A polymer concentration of less than 0.01 wt % is not preferred because the obtained film will lack dynamic strength. A concentration of greater than 10 wt % may be too high to achieve an adequate honeycomb structure. The compositional ratio of the polymer compound and phospholipid is preferably 1:1-1000:1, more preferably 10:1-500:1 and even more preferably 50:1-200:1. If the phospholipid is present at less than 1/1000 with respect to polymer compound, it may not be possible to obtain a homogeneous honeycomb structure. If the weight ratio is greater than 1:1, the film may not be self-supporting, while cost will be increased leading to economic disadvantages.

According to the invention, the polymer-organic solvent solution is cast onto a base to form a film with a honeycomb structure, where the base used may be an inorganic material such as glass, metal or a silicon wafer, a polymer with excellent organic solvent resistance such as polypropylene, polyethylene or polyetherketone, or a liquid such as water, liquid paraffin or liquid polyether. When water is used as the base, the self-standing property of the honeycomb structure is preferably utilized to allow the structure to be easily removed as a separate body from the base.

The mechanism by which the honeycomb structure is formed according to the invention is believed to be as follows. When the hydrophobic organic solvent evaporates it consumes latent heat and causes a temperature reduction on the cast film surface, resulting in coalescence and adhesion of fine water droplets on the polymer solution surface. The action of the hydrophilic portion of the polymer solution reduces surface tension between water and the hydrophobic organic solvent, and therefore the fine water droplets coalesce toward a single mass and are stabilized. As the solvent evaporates, hexagonally-formed liquid drops become arranged into their closest packing, and finally the water escapes leaving the polymer arranged in the form of a regular honeycomb shape. The environment for preparation of the film preferably has a relative humidity in the range of 10-95%. At less than 10% condensation of the water droplets on the cast film will be insufficient, and at greater than 95% it will be more difficult to maintain environmental control. The inner diameter of each of the honeycomb cavities of the honeycomb structure obtained in this method is from 0.1 to 100 μm. The cavity inner diameter suitable for cell culture is preferably 0.1-20 μm and even more preferably 1-15 μm. The film with a honeycomb structure produced in this method has the honeycomb structure on its surface, and if the film thickness is sufficiently large the back surface in contact with the base will be flat with no perforated holes. If the film thickness is smaller than the water droplet sizes, the resulting film will have perforated holes. A perforated or non-perforated film may be selected as appropriate for the intended use.

The tissue regeneration substrate of the invention is a particularly suitable substrate for regeneration of cartilage tissue. A cell culture method on a film with a honeycomb structure and a method for production of a tissue regeneration complex will now be described using chondrocytes as an exemplary model.

The chondrocytes used for culturing on the film with a honeycomb structure may be obtained from hyaline cartilage, fibrocartilage or elastic cartilage. For ideal repair of transplantation, it is preferred to use articular chondrocytes obtained from cartilage of joints that are not under a heavy weight load. The cells are prepared by extraction from tissue followed by removal of the connective tissue etc. by ordinary protocols. Primary culturing by an ordinary protocol may also be carried out for pre-growth of the cells.

When the chondrocytes are seeded in the film with a honeycomb structure according to the invention, the film with the honeycomb structure may be formed on a dish for direct use, or the film with the honeycomb structure may be inserted in a cell culturing vessel, depending on the most convenient method.

After seeding the cells on the film with the honeycomb structure, culturing solution is added and cultured growth may be carried out in a suitable medium in, for example, a 37° C., 5% $CO_2$ incubator.

The advantage of using a film with a honeycomb structure according to the invention is that the surface honeycomb structure results in a smaller cell adhesion area than a smooth film, such that cell growth is inhibited, a substrate is produced and the same effect is exhibited as a three-dimensional scaffold. Thus by using a film with a honeycomb structure it is possible to prevent changes in cellular morphology that occurs with repeated growth, and in the case of chondrocytes, for example, it is possible to lower the proportion of low cartilage substrate-producing fibrochondrocytes in the complex for cartilage tissue regeneration. As a result, reconstruction of cartilage tissue by chondrocytes can be accomplished more efficiently.

Moreover, using a film with a non-perforated honeycomb structure avoids leakage of the seeding cell suspension from the film, resulting in increased density of the retained cells compared to a three-dimensional sponge or the like, and allowing rapid and efficient tissue regeneration. When the cell-retaining complex is used in its film form it is possible to achieve regeneration of thin tissue, but cell-retaining complexes may also be laminated as shown in FIG. 1. In this case, the thickness of the regenerated tissue may be adjusted by the number of layers of laminated honeycomb structure films. Since cells are seeded in each of the honeycomb structure films, the density of cells in the laminated honeycomb structure films is the same as in a complex with a single film, and transplantation thereof into the body allows satisfactory tissue regeneration to take place. Depending on the site of tissue regeneration, lamination of films with different cell densities may even be possible. Also, the types of cells retained in the honeycomb structure films may be varied so that their lamination forms a structure approximating that found in the body.

Figure 2:
FIG. 2 shows an example of the form of a complex comprising a cartilage regeneration substrate and chondrocytes cultured on the substrate, according to the invention.

Alternatively, a honeycomb structure film covered with cells may be wound into a roll as shown in FIG. 2, to form a cylindrical shape. In this case, the size of the regenerated tissue can be adjusted by the height of the roll and the number of winds of the roll.

According to the invention, the cell seeding density for culturing on the honeycomb structure film will differ depending on the cell type, and for chondrocytes, for example, the preferred seeding density is one which favors cartilage substrate production over cell growth. Such a cell seeding density will allow the chondrocytes to abundantly produce the cartilage substrate from the start of culturing, to efficiently obtain a cartilage substrate in the amount necessary for cartilage regeneration.

For example, from the standpoint of more efficiently maintaining cellular morphology and producing cartilage substrate, the chondrocyte seeding density for the invention is in the range of $5 \times 10^4$ cells/ml to $1 \times 10^6$ cells/ml, and preferably in the range of $1 \times 10^5$ cells/ml to $8 \times 10^5$ cells/ml, for seeding of cells in an area of 400 $mm^2$, for example.

If the cell seeding density is lower than this range, growth of chondrocytes will be favored over cartilage substrate production, and the cellular morphology may be altered or a sufficient amount of cartilage substrate may not be efficiently produced. If the cell seeding density is higher than this range, the cellular activity of the chondrocytes may not be sufficiently maintained and production of cartilage substrate may be inadequate.

The cell culturing time may be in a range of 1 day to 4 weeks. The range is preferably from 3 days to 3 weeks, but this is not limitative because the culturing time may be varied based on the volume of cells seeded.

The cartilage substrate may consist of either or both substances normally produced by chondrocytes in the body and substances produced under the culturing conditions. As such substances there may be mentioned glycosaminoglycans (GAG) such as chondroitin sulfate, hyaluronic acid and keratan sulfate, or type II collagen. The amount of cartilage substrate can be measured by quantitation of GAG, for example.

Since the tissue regeneration graft of the invention therefore comprises numerous cells and abundant substrate, it is highly biocompatible and can efficiently accomplish tissue repair when transplanted.

As examples of conditions to be treated, wherein a complex of a tissue regeneration substrate and chondrocytes in which chondrocytes have been cultured according to the invention may be used as a graft, there may be mentioned cartilage damage, osteochondritis dissecans, osteoarthritis and rheumatoid arthritis, but there is no limitation to these conditions, and it may be applied for general conditions associated with loss of cartilage. Cells suitable for the tissue to be regenerated may be cultured on the tissue regeneration substrate to obtain a complex for use in tissue regeneration.

EXAMPLES

The present invention will now be explained in greater detail by examples, with the understanding that the invention is in no way limited by the examples.

Example 1

Figure 3:
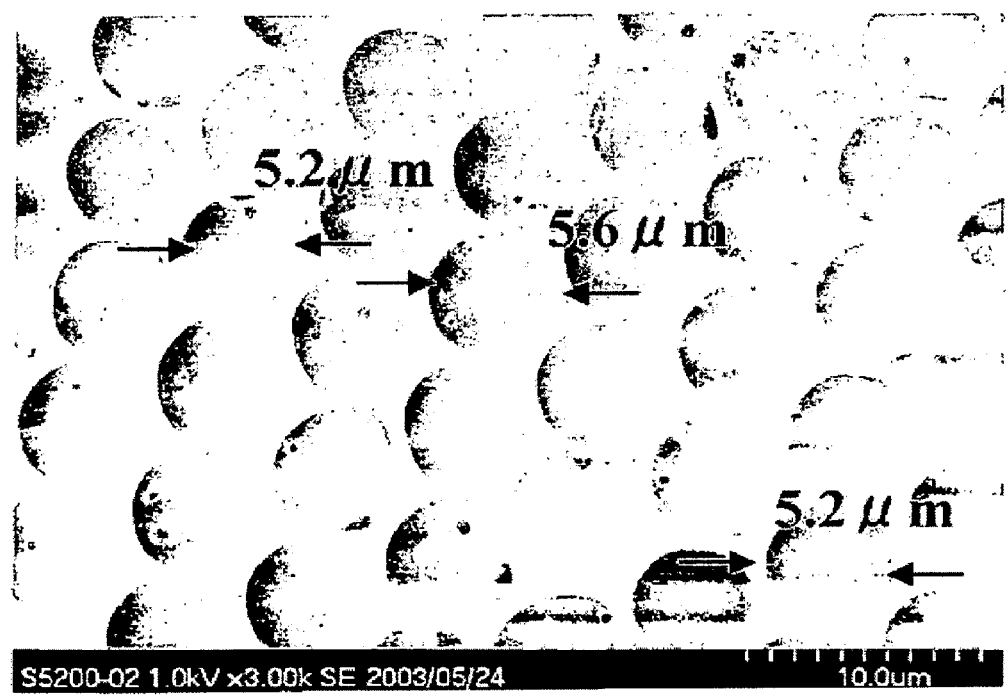
FIG. 3 is an electron micrograph showing the film with a honeycomb structure obtained in Example 1.

In a solution of polylactic acid (trade name: "Lacty9031" by Shimadzu Laboratories, weight-average molecular weight: 168,000) in chloroform (5 g/L) there was mixed phosphatidylethanolamine-dioleoyl (Wako Pure Chemical Industries Co., Ltd.) as a surfactant in a proportion of 200:1, and the mixture was cast onto a glass panel and allowed to stand at room temperature, 70% humidity for gradual escape of the solvent to prepare a film with a honeycomb structure. An electron micrograph thereof is shown in FIG. 3, indicating that a honeycomb film with an average cavity inner diameter of about 5 μm had been obtained.

Example 2

Figure 4:
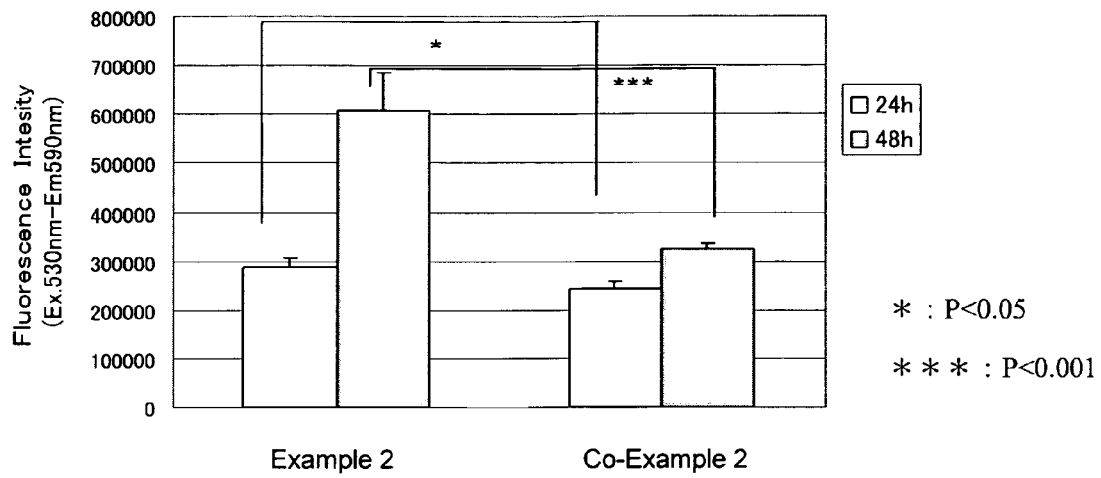
FIG. 4 shows the results of metabolic activity measurement for Example 2 and Comparative Example 2.

The film with a honeycomb structure fabricated in Example 1 was sterilized with 70% ethanol and the film was inserted in a sterilized cell culturing vessel (diameter: 15 mm). A 0.5 ml portion of mouse fetal fibroblasts (NIH3T3 cells) (ATCC) at $3.6 \times 10^4$ cells/ml were seeded on the film and culturing was conducted in D-MEM serum medium in a 37° C., 5% $CO_2$ incubator. After 24 and 48 hours, the metabolic activity of the cells was measured by the Alamar Blue method, using excitation light at a wavelength of 530 nm and detection of emerging fluorescence at 590 nm. The results are shown in FIG. 4. (In FIG. 4, p represents the P value (probability value)).

Comparative Example 1

Figure 5:
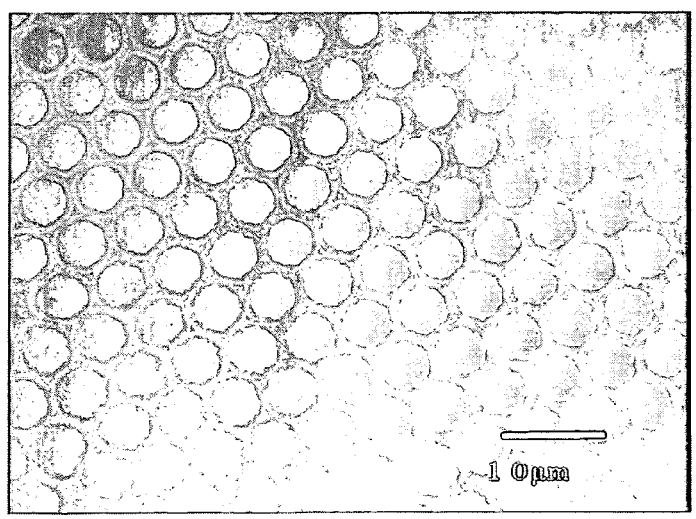
FIG. 5 is an electron micrograph showing the film with a honeycomb structure obtained in Comparative Example 1.

In a solution of polylactic acid in chloroform (5 g/L) there was mixed a polyacrylamide polymer (weight-average molecular weight: 85,000) prepared by the process described in Japanese Unexamined Patent Publication No. 2001-157574 as a surfactant in a proportion of 10:1, and the mixture was cast onto a glass panel and allowed to stand at room temperature, 70% humidity for gradual escape of the solvent to prepare a film with a honeycomb structure. An electron micrograph of the obtained film is shown in FIG. 5, indicating that a honeycomb film with an average cavity inner diameter of about 5 μm had been obtained.

Comparative Example 2

A test was conducted in the same method as Example 2 using the film fabricated in Comparative Example 1. The results are shown in FIG. 4.

As seen in FIG. 4, the tissue regeneration substrate of Example 1 composed of polylactic acid and a phospholipid exhibited higher metabolic activity than the tissue regeneration substrate of Comparative Example 1 composed of polylactic acid and an amphipathic polymer.

Example 3

The honeycomb structure film fabricated in Example 1 was sterilized with 70% ethanol and inserted in a sterilized cell culturing vessel. Separately, a thin cartilage strip was shaved off from rabbit knee articular cartilage with a scalpel and finely diced, after which it was enzyme treated for 1 hour in PBS(−) containing 0.15 (w/v) % trypsin, and then incubated at 37° C. for 2 hours and 30 minutes in PBS(−) containing 0.15 (w/v) collagenase. The filtrate obtained by filtration using a nylon filter with a pore size of 70 μm was centrifuged for 3 minutes at 1500 rpm and rinsed twice with α-MEM serum medium containing an antibiotic and 10% fetal calf serum, after which the rabbit knee chondrocytes were obtained. The chondrocytes were cultured in α-MEM serum medium in a 37° C., 5% $CO_2$ incubator. Chondrocytes from the second subculturing were detached and collected with 0.25% trypsin/1 mmol EDTA/PBS(−), and a $2\times10^5$ cell/ml cell solution was prepared. After wetting the honeycomb structure film with 1 ml of medium, 1 ml of the cell solution was seeded therein. It was then housed in a 6-well plate and cultured in a 5% $CO_2$, 37° C. incubator. The entire medium was aspirated on the following day and exchanged with 2 ml of 25 μg/ml ascorbic acid-containing medium added to the cell culturing vessel, after which the medium was exchanged every 2 days and culturing was performed by allowing the mixture to stand for up to 3 weeks. At 3 and 10 day points, the metabolic activity of the cells was measured by the Alamar Blue method. The results are shown in Table 1. After culturing, the graft was removed from the vessel and the GAG content was measured using a Blyscan™ kit by Biocolor (UK) The results are shown in Table 2.

Figure 6:
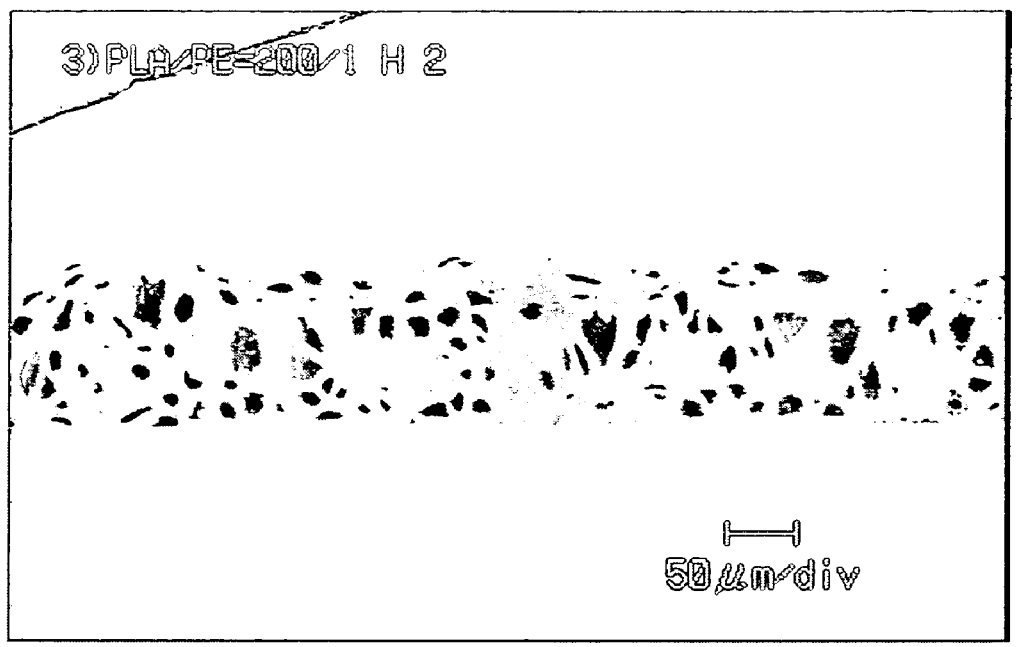
FIG. 6 is an optical micrograph showing the complex of chondrocytes and a cartilage tissue regeneration substrate obtained in Example 3.

An optical micrograph of the obtained complex of chondrocytes and cartilage tissue regeneration substrate is shown in FIG. 6.

Comparative Example 3

The film fabricated in Comparative Example 1 was used for culturing in the same method as Example 3. At 3 and 10 day points, the metabolic activity of the cells was measured by the Alamar Blue method. The results are shown in Table 1.

TABLE 1

| | Fluorescent intensity | |
|---|---|---|
| | At 3 days | At 10 days |
| Example 3 | 40549 | 1763476 |
| Comp. Example 3 | 31221 | 1320767 |

The metabolic activity test demonstrated that the tissue regeneration substrate made of a film composed of polylactic acid and a phospholipid obtained in Example 1 exhibits higher metabolic activity than the tissue regeneration substrate made of a film composed of polylactic acid and an amphipathic polymer obtained in Comparative Example 1.

Comparative Example 4

Chondrocytes were cultured (monolayer culture) in the same method on a dish of the same size as Example 3, and the GAG content was measured after 3 weeks of culturing. The results are shown in Table 2.

Comparative Example 5

In the same method as Example 3, rabbit chondrocytes were extracted and combined with culturing medium to prepare a chondrocyte suspension, and the chondrocyte suspension was embedded in an equal amount of collagen (atelocollagen: Koken Co., Ltd.) at a density of $2\times10^5$ cells/ml, upon which culturing was initiated. The final collagen concentration was 2.4 wt %. This was then housed in a 6-well plate and cultured in a 5% $CO_2$, 37° C. incubator using medium containing 25 μg/ml ascorbic acid, and the GAG content was measured after 3 weeks of culturing. The results are shown in Table 2.

TABLE 2

| | GAG contents of cells |
|---|---|
| | GAG content (μg/μg DNA) |
| Example 3 (honeycomb structure film) | 102 |
| Comparative Example 4 (monolayer culture) | 49 |
| Comparative Example 5 (atelocollagen gel) | 28 |

As shown in Table 2, the amount of GAG synthesis in the honeycomb structure film was over twice that found with monolayer culture, and almost 4 times that found with atelocollagen gel culture. As mentioned above, the GAG content reflects the amount of cartilage substrate, and therefore Example 3 had a greater amount of cartilage substrate production.

Comparative Example 6

A cast film was prepared by mixing a solution of polylactic acid in chloroform (5 g/L) with L-α-phosphatidylethanolamine-dioleoyl as a surfactant in a proportion of 200:1, casting it onto a glass panel and allowing it to stand at room temperature for gradual escape of the solvent.

Comparative Example 7

Figure 7:
FIG. 7 is an optical micrograph showing the complex of chondrocytes and a cartilage tissue regeneration substrate obtained in Comparative Example 7.

Chondrocytes were cultured under the same conditions as Example 3 on a cast film obtained for Comparative Example 6. FIG. 7 shows an optical micrograph of the obtained chondrocyte and cast film complex.

FIGS. 6 and 7 demonstrate that with a tissue regeneration substrate made of a film with a honeycomb structure according to the invention, the chondrocytes grow three-dimensionally, without alteration in cellular morphology, i.e. with a low amount of fibrous cartilage, whereas with the tissue regeneration substrate composed of a simple cast film, the result was low production of extracellular substrate and flattening of cells, i.e. fibrous cartilage.

What is claimed is:

1. A tissue regeneration substrate comprising a film with a honeycomb structure having an average cavity inner diameter from 0.1 to 20 µm, consisting essentially of (a) one or more polymers selected from the group consisting of polylactic acid, (lactic acid-glycolic acid) copolymer, polyhydroxybutyric acid, polycaprolactone, biodegradable aliphatic polyesters, aliphatic polycarbonate, and their copolymers and (b) a phospholipid.

2. A tissue regeneration substrate according to claim 1, wherein said phospholipid is at least one type selected from the group consisting of phosphatidylethanolamine, phosphatidylcholine, phosphatidylserine, phosphatidylglycerol and their derivatives.

3. A tissue regeneration substrate according to claim 2, wherein said phospholipid is phosphatidylethanolamine.

4. A tissue regeneration substrate according to claim 2, wherein said phospholipid is L-α-phosphatidylethanolamine-dioleoyl.

5. A tissue regeneration substrate according to claim 1, characterized in that the compositional ratio of the polymer and the phospholipid is 10:1 to 500:1 by weight.

6. A tissue regeneration substrate according to claim 1, characterized in that the tissue is cartilage tissue.

7. A tissue regeneration complex comprising a tissue regeneration substrate according to claim 1 and cells held in said tissue regeneration substrate.

8. A tissue regeneration complex according to claim 7, characterized in that the tissue is cartilage tissue.

9. A method for production of a tissue regeneration complex comprising cells held on a tissue regeneration substrate, by culturing cells on a tissue regeneration substrate according to claim 1.

10. A tissue regeneration substrate according to claim 1, comprising a film with a honeycomb structure having an average cavity inner diameter from 0.1 to 20 µm, consisting essentially of (a) polylactic acid and (b) a phospholipid.

11. A tissue regeneration substrate according to claim 1, comprising a film with a honeycomb structure having an average cavity inner diameter from 0.1 to 20 µm, consisting essentially of (a) (lactic acid-glycolic acid) copolymer and (b) a phospholipid.

12. A tissue regeneration substrate according to claim 1, comprising a film with a honeycomb structure having an average cavity inner diameter from 0.1 to 20 µm, consisting essentially of (a) polycaprolactone and (b) a phospholipid.

13. A tissue regeneration substrate according to claim 1, comprising a film with a honeycomb structure having an average cavity inner diameter from 0.1 to 20 µm, consisting essentially of (a) polylactic acid-polycaprolactone copolymer and (b) a phospholipid.

14. A tissue regeneration substrate according to claim 5, wherein the compositional ratio of the polymer and the phospholipid is 50:1 to 200:1 by weight.

15. A tissue regeneration substrate comprising a film with a honeycomb structure having an average cavity inner diameter from 0.1 to 20 µm, composed primarily of (a) one or more polymers selected from the group consisting of polylactic acid, (lactic acid-glycolic acid) copolymer, polyhydroxybutyric acid, polycaprolactone, biodegradable aliphatic polyesters, aliphatic polycarbonate, and their copolymers and (b) a phospholipids, wherein no amphipathic polymer is present.

* * * * *